United States Patent
Shin

(10) Patent No.: US 10,638,068 B2
(45) Date of Patent: Apr. 28, 2020

(54) ENDOSCOPE AND ENDOSCOPE SYSTEM

(71) Applicant: OLYMPUS CORPORATION, Tokyo (JP)

(72) Inventor: Hidetoshi Shin, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 271 days.

(21) Appl. No.: 15/478,857

(22) Filed: Apr. 4, 2017

(65) Prior Publication Data

US 2017/0208268 A1 Jul. 20, 2017

Related U.S. Application Data

(63) Continuation of application No. PCT/JP2015/075634, filed on Sep. 9, 2015.

(30) Foreign Application Priority Data

Dec. 19, 2014 (JP) .................. 2014-256941

(51) Int. Cl.
*H04N 5/357* (2011.01)
*H04N 5/365* (2011.01)
(Continued)

(52) U.S. Cl.
CPC .............. *H04N 5/357* (2013.01); *A61B 1/04* (2013.01); *A61B 1/045* (2013.01);
(Continued)

(58) Field of Classification Search
CPC ........ H04N 5/357; H04N 5/2256; A61B 1/04; A61B 1/045; G02B 23/2484
(Continued)

(56) References Cited

U.S. PATENT DOCUMENTS 8,462,235 B2 6/2013 Moore
2004/0143157 A1* 7/2004 Doguchi ............ A61B 1/00059
600/109
(Continued)

FOREIGN PATENT DOCUMENTS

CN 101268682 A 9/2008
CN 102761712 A 10/2012
(Continued)

OTHER PUBLICATIONS

Extended Supplementary European Search Report dated Jun. 12, 2018 in European Patent Application No. 15 86 9612.0.
(Continued)

*Primary Examiner* — Sath V Perungavoor
*Assistant Examiner* — Kristin Dobbs
(74) *Attorney, Agent, or Firm* — Scully, Scott, Murphy & Presser, P.C.

(57) ABSTRACT

An endoscope includes: pixels arranged in a matrix form and configured to generate an imaging signal according to an amount of received light, and output the imaging signal through one of vertical lines in the pixels, each two pixels adjacent to one another in a horizontal direction sharing a single vertical line; dummy pixels, each provided for each vertical line in the pixels; a determination unit for determining whether output values of dummy signals having been output multiple times from a dummy pixel of the dummy pixels, are within a range of a threshold; a correction data generator configured to: calculate, for each vertical line, a statistic of the output values of the dummy signals determined to be within the range of the threshold; and generate, for each vertical line, correction data based on the calculation; and a correction unit for correcting the imaging signal based on the correction data.

5 Claims, 11 Drawing Sheets

(51) Int. Cl.
  *H04N 5/361* (2011.01)
  *H04N 5/374* (2011.01)
  *A61B 1/045* (2006.01)
  *A61B 1/04* (2006.01)
  *G02B 23/24* (2006.01)
  *H04N 5/225* (2006.01)

(52) U.S. Cl.
  CPC ....... *G02B 23/2484* (2013.01); *H04N 5/2256* (2013.01); *H04N 5/361* (2013.01); *H04N 5/3651* (2013.01); *H04N 5/3658* (2013.01); *H04N 5/374* (2013.01); *H04N 2005/2255* (2013.01)

(58) Field of Classification Search
  USPC .......................................................... 348/68
  See application file for complete search history.

(56) References Cited

U.S. PATENT DOCUMENTS

| | | | |
|---|---|---|---|
| 2006/0044424 A1 | 3/2006 | Shirai et al. | |
| 2006/0176519 A1 | 8/2006 | Ouchi | |
| 2007/0019085 A1* | 1/2007 | Suzuki | H04N 5/361 |
| | | | 348/241 |
| 2010/0231762 A1 | 9/2010 | Shirai et al. | |
| 2011/0025874 A1 | 2/2011 | Tamaoki | |
| 2012/0092473 A1 | 4/2012 | Takamatsu | |
| 2012/0274823 A1* | 11/2012 | Matsuda | H04N 5/3532 |
| | | | 348/302 |
| 2014/0139643 A1 | 5/2014 | Hogasten et al. | |
| 2014/0320618 A1 | 10/2014 | Akahane et al. | |

FOREIGN PATENT DOCUMENTS

| | | |
|---|---|---|
| JP | 2006-74172 A | 3/2006 |
| JP | 2008-206003 A | 9/2008 |
| JP | 2010-136101 A | 6/2010 |
| JP | 2011-30097 A | 2/2011 |
| JP | 2011-41255 A | 2/2011 |
| JP | 2012-85715 A | 5/2012 |
| JP | 2012-147163 A | 8/2012 |
| JP | 2013-62601 A | 4/2013 |
| JP | 2013-219558 A | 10/2013 |

OTHER PUBLICATIONS

Japanese Office Action dated Aug. 31, 2016 received in JP 2016-548326.
International Search Report dated Nov. 10, 2015 received in PCT/JP2015/075634.
Chinese Office Action dated Jul. 31, 2019 in Chinese Patent Application No. 201580056214.3.

* cited by examiner

246a

246b

ONE FRAME

DUMMY SIGNAL LINE — a1

IMAGING SIGNAL LINE

W1

ENDOSCOPE AND ENDOSCOPE SYSTEM

CROSS REFERENCES TO RELATED APPLICATIONS

This application is a continuation of PCT international application Ser. No. PCT/JP2015/075634, filed on Sep. 9, 2015 which designates the United States, incorporated herein by reference, and which claims the benefit of priority from Japanese Patent Application No. 2014-256941, filed on Dec. 19, 2014, incorporated herein by reference.

BACKGROUND

1. Technical Field

The disclosure relates to an endoscope configured to be introduced into a living body to acquire images in the living body. The disclosure also relates to an endoscope system including the endoscope.

2. Related Art

Solid state image sensors each having a plurality of pixels are configured to receive light and perform photoelectric conversion on the light and output an electrical signal. It has been known that, in an image captured by a solid state image sensor, vertical stripe noise occurs due to variation in characteristics of elements in a column circuit. In order to address this situation, a technique has been known in which an effective pixel area for receiving light and an optical black area where light receiving surfaces of pixels are shielded by an aluminum thin film are provided, and an output value of the effective pixel area is corrected based on an output value from the pixels of the optical black area (see JP 2011-41255 A).

SUMMARY

In some embodiments, an endoscope includes a plurality of pixels arranged in a two-dimensional matrix form and configured to receive light from outside, generate an imaging signal according to an amount of received light, and output the imaging signal through one of a plurality of vertical lines in the plurality of pixels, each two pixels adjacent to one another in a horizontal direction among the plurality of pixels sharing a single vertical line of the plurality of vertical lines; a plurality of dummy pixels, each of which is provided for each of the plurality of vertical lines in the plurality of pixels and is configured to generate and output a dummy signal to be used for correction processing of the imaging signal; a threshold recording unit configured to record a threshold; a determination unit configured to determine whether or not each of output values of dummy signals having been output a plurality of times from a dummy pixel of the plurality of dummy pixels, is within a range of the threshold; a correction data generator configured to: calculate, for each of the plurality of vertical lines, a statistic of the output values of the dummy signals determined to be within the range of the threshold by the determination unit; generate, for each of the plurality of vertical lines, correction data for correcting the imaging signal generated by each two pixels sharing the single vertical line, based on a result of calculation; generate a new threshold by using the output values of the dummy signals; and cause the threshold recording unit to record the new threshold for updating; and a correction unit configured to correct the imaging signal based on the correction data generated by the correction data generator.

In some embodiments, an endoscope system includes the endoscope according, and a processing device configured to convert the imaging signal into an image signal. The endoscope includes the correction data generator, the correction unit, and a connector unit configured to be connected to the processing device.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, an endoscope system including an imaging device will be described as modes for carrying out the present invention (hereinafter referred to as "embodiment(s)"). The present invention is not limited by the embodiments. The same reference signs are used to designate the same elements throughout the drawings. The drawings are schematic and, accordingly, a relationship between the thickness and the width of each member and ratios of members are different from actual ones. Dimensions and ratios of members may be different between the drawings.

First Embodiment

Configuration of Endoscope System

Figure 1:
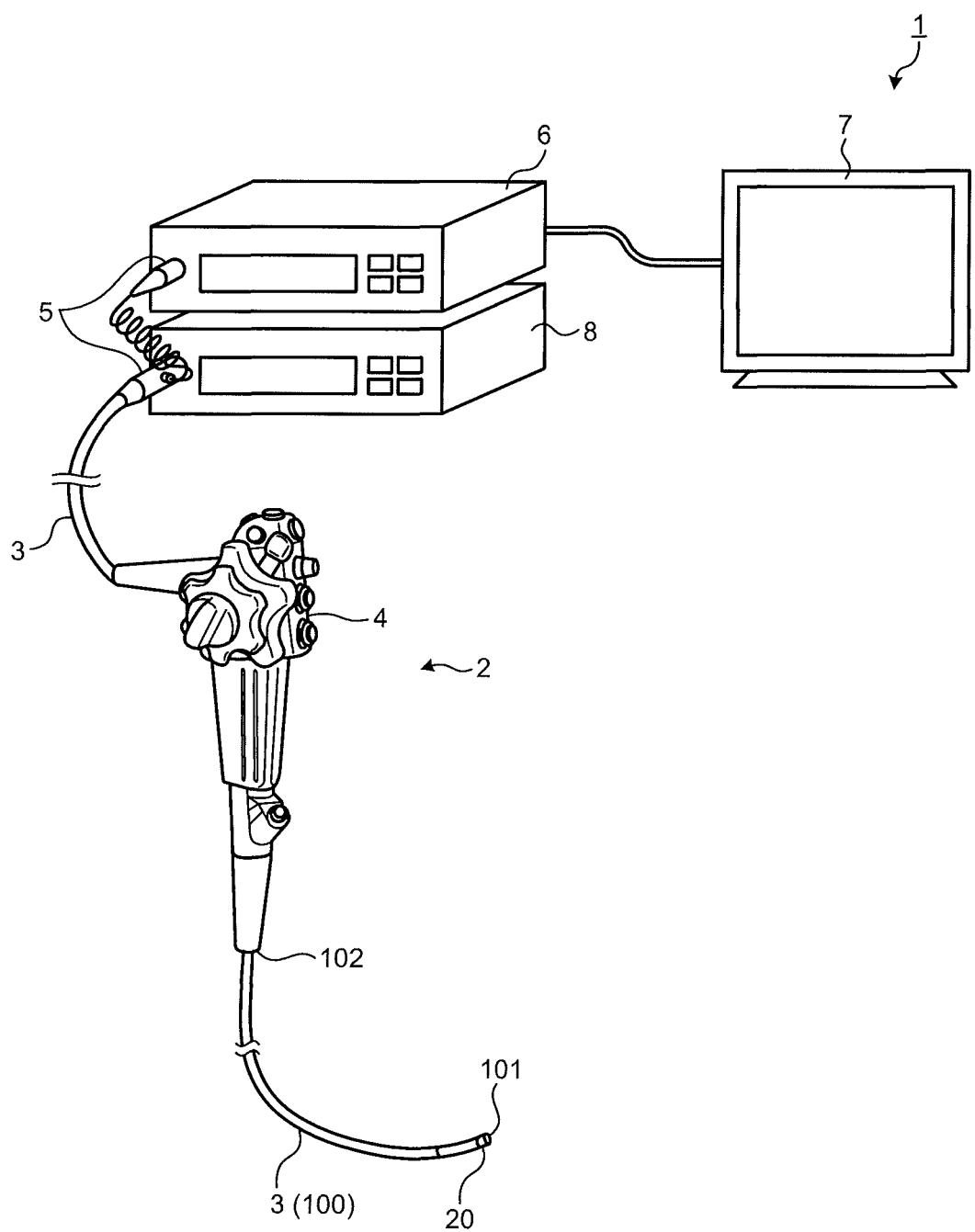
FIG. 1 is a diagram schematically illustrating an entire configuration of an endoscope system according to a first embodiment of the present invention.

FIG. 1 is a diagram schematically illustrating an entire configuration of an endoscope system according to a first embodiment of the present invention. An endoscope system 1 illustrated in FIG. 1 includes an endoscope 2, a transmission cable 3, a connector unit 5, a processor 6 (processing device), a display device 7, and a light source device 8.

When an insertion portion 100 which is a part of the transmission cable 3 is inserted into a body cavity of a subject, the endoscope 2 captures in-vivo images of the subject and outputs an imaging signal (image data) to the processor 6. In the endoscope 2, an imaging unit 20 (an imaging device) that captures in-vivo images is provided to one end of the transmission cable 3, which is a distal end 101 of the insertion portion 100 to be inserted into a body cavity of the subject, and an operating unit 4 that receives various operations to be performed on the endoscope 2 is connected to a proximal end 102 of the insertion portion 100. The imaging unit 20 is connected to the connector unit 5 by the transmission cable 3 through the operating unit 4. An imaging signal of images captured by the imaging unit 20 is output to the connector unit 5 through the transmission cable 3 having a length of, for example, several meters.

The connector unit 5 is connected to the endoscope 2, the processor 6, and the light source device 8. The connector unit 5 performs predetermined signal processing on the imaging signal outputted by the connected endoscope 2, converts (A/D-converts) the imaging signal from an analog signal to a digital signal, and outputs the digital signal to the processor 6 as an image signal.

The processor 6 performs predetermined image processing on the image signal outputted from the connector unit 5 and integrally controls the entire endoscope system 1. In the first embodiment, the processor 6 functions as a processing device.

The display device 7 displays an image corresponding to the image signal on which the processor 6 performs the image processing. The display device 7 displays various information related to the endoscope system 1.

The light source device 8 is configured using, for example, a halogen lamp, a white LED (Light Emitting Diode), or the like. The light source device 8 emits illumination light to the subject from the distal end 101 of the insertion portion 100 of the endoscope 2 through the connector unit 5 and the transmission cable 3.

Figure 2:
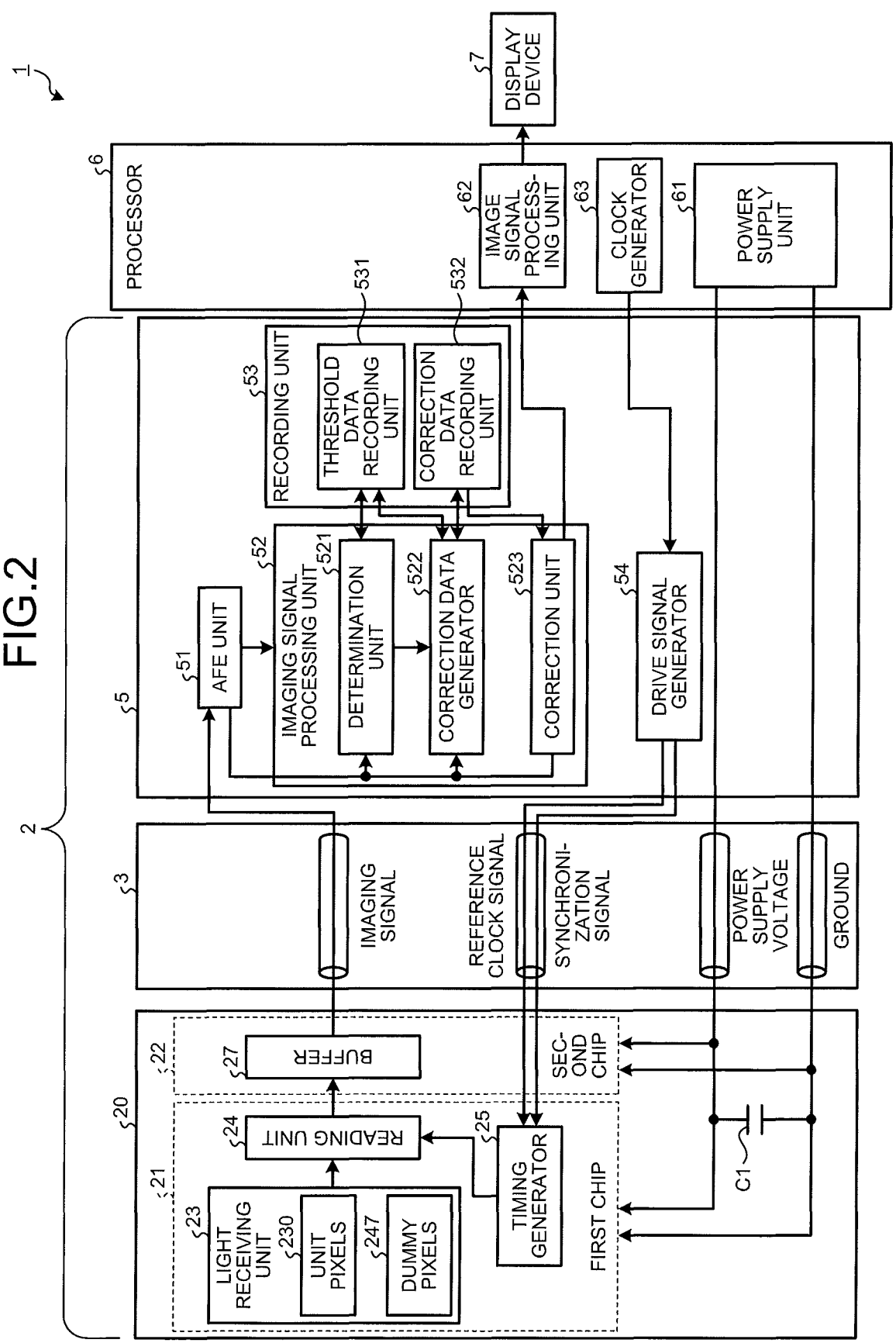
FIG. 2 is a block diagram illustrating functions of main parts of the endoscope system according to the first embodiment of the present invention.

FIG. 2 is a block diagram illustrating functions of main parts of the endoscope system 1. Details of each element of the endoscope system 1 and paths of electrical signals in the endoscope system 1 will be described with reference to FIG. 2.

As illustrated in FIG. 2, the imaging unit 20 includes a first chip 21 (an image sensor) and a second chip 22.

The first chip 21 includes: a light receiving unit 23 including a plurality of unit pixels 230 which is arranged in a two-dimensional matrix form in row and column directions and which receives light from outside and generates and outputs an imaging signal according to the amount of received light and a plurality of dummy pixels 247 which is provided for each vertical line in the arrangement of the plurality of unit pixels 230 and which generates and outputs a dummy signal used for correction processing of the imaging signal; a reading unit 24 that reads the imaging signal and the dummy signal that are photoelectrically converted by the light receiving unit 23; and a timing generator 25 that generates a timing signal based on a reference clock signal and a synchronization signal that are input from the connector unit 5 and outputs the timing signal to the reading unit 24. A more detailed configuration of the first chip 21 will be described later with reference to FIG. 3.

The second chip 22 has a buffer 27 that functions as a transmitting unit that transmits the imaging signal outputted from the first chip 21 to the processor 6 through the transmission cable 3 and the connector unit 5. A combination of circuits mounted on the first chip 21 and the second chip 22 can be appropriately changed according to convenience of setting.

The imaging unit 20 receives a power supply voltage VDD generated by a power supply unit 61 in the processor 6 through the transmission cable 3 along with a ground GND. A capacitor C1 for power supply stabilization is provided between the power supply voltage VDD and the ground GND that are supplied to the imaging unit 20.

The connector unit 5 has an analog-front-end unit 51 (hereinafter referred to as "AFE unit 51"), an imaging signal processing unit 52, a recording unit 53, and a drive signal generator 54. The connector unit 5 functions as a relay processing unit that electrically connects the endoscope 2 (the imaging unit 20) with the processor 6 and relays an electrical signal. The connector unit 5 and the imaging unit 20 are connected by the transmission cable 3 and the connector unit 5 and the processor 6 are connected by, for example, a coil cable. The connector unit 5 is connected also to the light source device 8.

The AFE unit 51 receives the imaging signal transmitted from the imaging unit 20 and performs impedance matching by using a passive element such as a resistor, and thereafter, extracts AC components by using a capacitor and determines an operating point by a partial resistance. Thereafter, the AFE unit 51 analog-digital (A/D) converts an analog imaging signal into a digital imaging signal and sends the digital imaging signal to the imaging signal processing unit 52.

The imaging signal processing unit 52 includes, for example, an FPGA (Field Programmable Gate Array). The imaging signal processing unit 52 generates a reference clock signal (for example, a clock of 27 MHz) to be a reference of an operation of each element of the endoscope 2 and a synchronization signal representing a start position of each frame and supplies the reference clock signal and the synchronization signal to the timing generator 25. Further, the imaging signal processing unit 52 performs predetermined signal processing such as noise removal on the digital imaging signal input from the AFE unit 51.

Here, a detailed configuration of the imaging signal processing unit 52 will be described. The imaging signal processing unit 52 has at least a determination unit 521, a correction data generator 522, and a correction unit 523.

The determination unit 521 determines whether or not each of output values of the dummy signals, which have been output a plurality of times from the dummy pixel 247, is within a predetermined range. Specifically, the determination unit 521 determines whether or not each of output values of the dummy signals, which have been output a plurality of times from the dummy pixel 247, is within a predetermined range from a threshold based on the threshold recorded by a threshold data recording unit 531 described later. The threshold is a value obtained by a normal dummy pixel 247, in advance, by an experiment or the like.

The correction data generator 522 calculates a statistic of output values of dummy signals, which have been determined to be within the predetermined range by the determination unit 521, for each vertical line. Subsequently, the correction data generator 522 generates correction data for correcting the imaging signal outputted by the unit pixels 230 based on a result of the calculation for each vertical line, and causes a correction data recording unit 532, which will be described later, to record the correction data. Here, the statistic is any one of an average value, a median value, and a mode value of the output values of dummy signals, which have been determined to be within the predetermined range by the determination unit 521, for each vertical line. In the description below, a case will be described in which the average value is used as the statistic. Further, the correction data generator 522 generates correction data for each frame in which each of the plurality of unit pixels 230 generates an imaging signal, with respect to the output values of dummy signals which have been determined to be within the predetermined range by the determination unit 521, and causes the correction data recording unit 532 to record the correction data. Furthermore, the correction data generator 522 calculates, for each vertical line, the sum of the output values of dummy signals, which have been determined to be within the predetermined range by the determination unit 521, divides the sum by the number of times of the addition of the output values to generate a threshold, and records the threshold in the threshold data recording unit 531 for updating.

The correction unit 523 corrects the imaging signal outputted by the unit pixels 230 based on the correction data generated by the correction data generator 522 and transmits the corrected imaging signal to an image signal processing unit 62 of the processor 6 described later. Specifically, the correction unit 523 corrects the imaging signal by subtracting correction data of a corresponding vertical line from the imaging signal outputted by the unit pixels 230 of each vertical line based on the correction data of each vertical line recorded by the correction data recording unit 532, and transmits the corrected imaging signal to the image signal processing unit 62.

The recording unit 53 records various information related to the endoscope 2. The recording unit 53 is configured using a Flash memory, a RAM (Random Access Memory), and the like. The recording unit 53 has the threshold data recording unit 531 that records threshold data used when the determination unit 521 determines whether or not an output value outputted from the dummy pixel 247 of the light receiving unit 23 is normal and the correction data recording unit 532 that records correction data of each vertical line of the imaging unit 20, which is generated by the correction data generator 522. Further, the correction data recording unit 532 records the output values of dummy signals which have been determined to be within the predetermined range by the determination unit 521 for each frame in which each of the plurality of unit pixels 230 generates an imaging signal (for each frame generated by the imaging unit 20).

The drive signal generator 54 generates a synchronization signal representing a start position of each frame based on the reference clock signal supplied from the processor 6 (for example, a clock signal of 27 MHz) to be a reference of an operation of each element of the endoscope 2 and outputs the synchronization signal along with the reference clock signal to the timing generator 25 of the imaging unit 20 through the transmission cable 3. Here, the synchronization signal generated by the drive signal generator 54 includes a horizontal synchronization signal and a vertical synchronization signal.

The processor 6 is a control device that integrally controls the entire endoscope system 1. The processor 6 includes a power supply unit 61, an image signal processing unit 62, and a clock generator 63.

The power supply unit 61 generates the power supply voltage VDD and supplies the generated power supply voltage VDD along with the ground GND to the imaging unit 20 through the connector unit 5 and the transmission cable 3.

The image signal processing unit 62 performs image processing such as synchronization processing, white balance (WB) adjustment processing, gain adjustment processing, gamma correction processing, digital/analog (D/A) conversion processing, and format conversion processing on the digital imaging signal on which the signal processing has been performed by the imaging signal processing unit 52. Thereby, the image signal processing unit 62 converts the digital imaging signal into an image signal and then outputs the image signal to the display device 7.

The clock generator 63 outputs the reference clock signal to the drive signal generator 54.

The display device 7 displays an image captured by the imaging unit 20 based on the image signal input from the image signal processing unit 62. The display device 7 is configured using a display panel such as a liquid crystal display panel or an organic EL (Electro Luminescence) display panel.

Configuration of First Chip

Next, a detailed configuration of the first chip 21 described above will be described.

Figure 3:
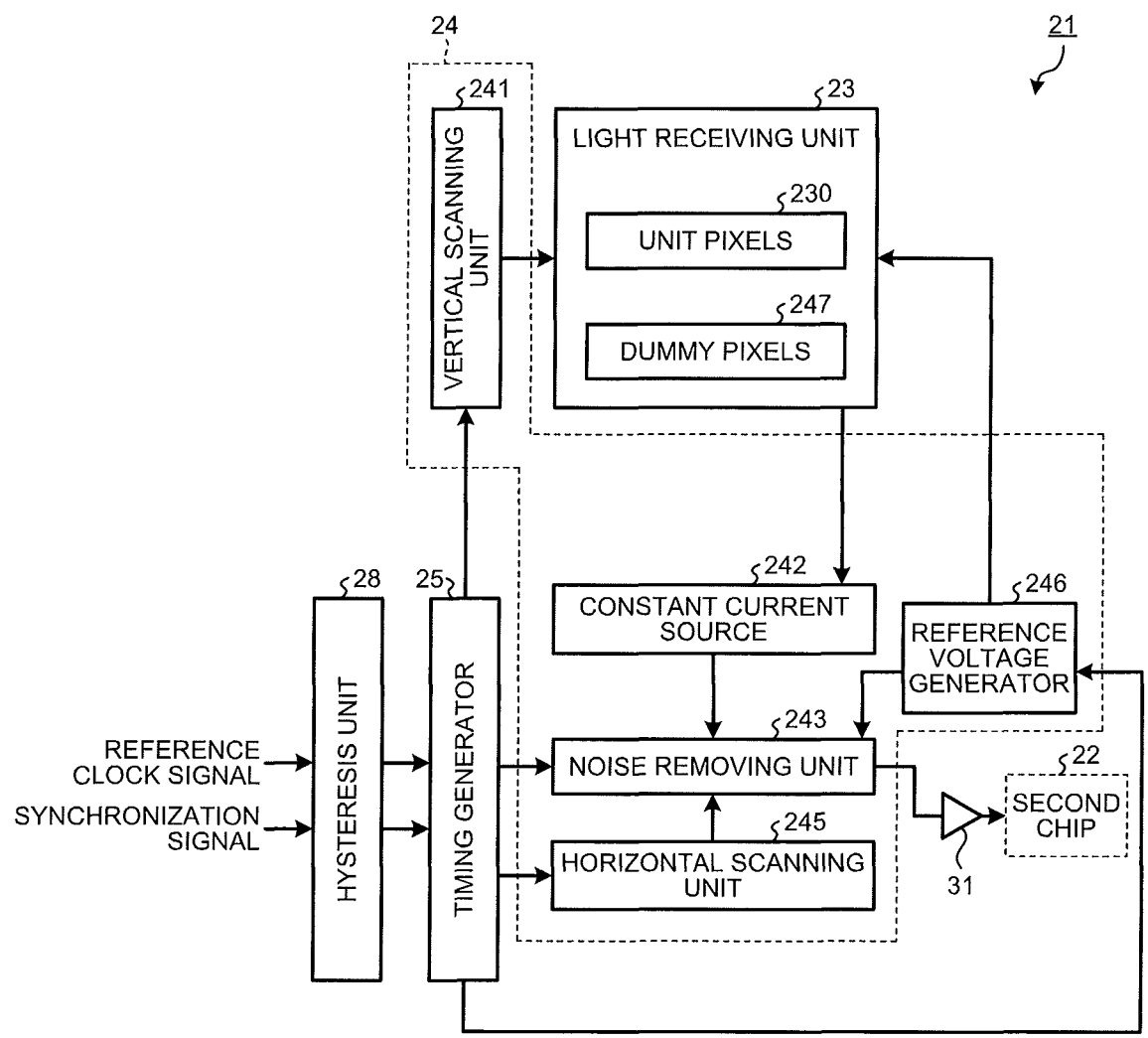
FIG. 3 is a block diagram illustrating a detailed configuration of a first chip according to the first embodiment of the present invention.
Figure 4:
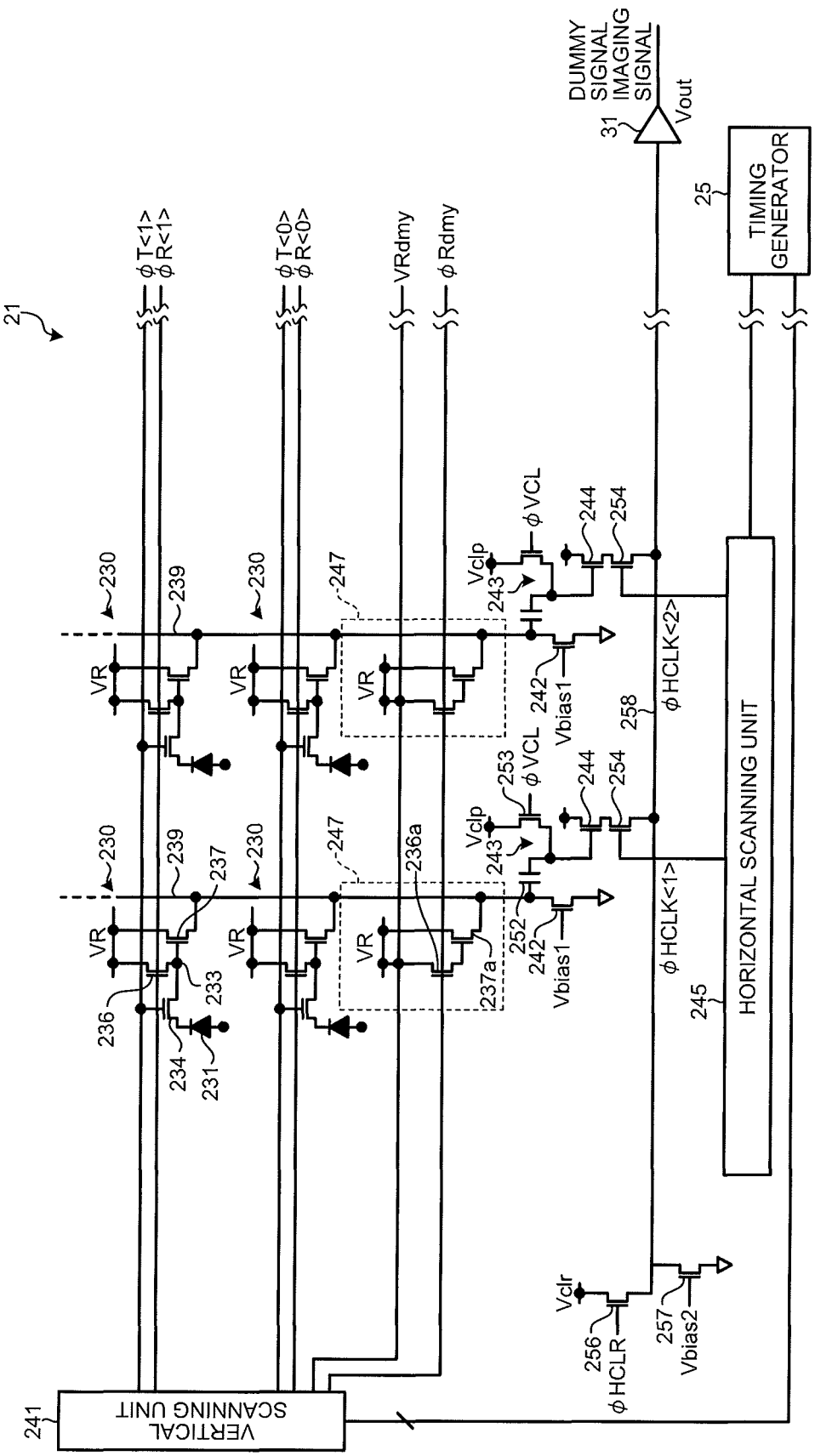
FIG. 4 is a circuit diagram illustrating a configuration of the first chip of the endoscope system according to the first embodiment of the present invention.

FIG. 3 is a block diagram illustrating the detailed configuration of the first chip 21 illustrated in FIG. 2. FIG. 4 is a circuit diagram illustrating the configuration of the first chip 21.

As illustrated in FIGS. 3 and 4, the first chip 21 has the light receiving unit 23, the reading unit 24 (drive unit), the timing generator 25, a hysteresis unit 28, and an output unit 31 (amplifier).

The hysteresis unit 28 shapes waveforms of the reference clock signal and the synchronization signal that are input through the transmission cable 3 and outputs the reference clock signal and the synchronization signal whose waveforms are shaped to the timing generator 25.

The timing generator 25 generates various drive signals based on the reference clock signal and the synchronization signal that are input from the hysteresis unit 28 and outputs the various drive signals to each of a vertical scanning unit 241 (row selection circuit), a noise removing unit 243, and a horizontal scanning unit 245 of the reading unit 24 described below.

The reading unit 24 transfers each of the imaging signal outputted from each of a plurality of pixels of the light receiving unit 23, which will be described later, and the reference signal outputted from a reference voltage generator 246 to the output unit 31.

Here, a detailed configuration of the reading unit 24 will be described. The reading unit 24 includes the vertical scanning unit 241 (row selection circuit), a constant current source 242, the noise removing unit 243 (noise removing circuit), a column source follower transistor 244, the horizontal scanning unit 245, and the reference voltage generator 246.

The vertical scanning unit 241 applies drive signals $\Phi T\langle M\rangle$ and $\Phi R\langle M\rangle$ to a selected row (horizontal line) $\langle M\rangle$ (M=0, 1, 2, . . . , m-1, and m) of the light receiving unit 23, based on drive signals ($\Phi T$, $\Phi R$, VRdmy, $\Phi$Rdmy, and the like) input from the timing generator 25. Then, the vertical scanning unit 241 cause the constant current source 242 to drive each of the unit pixels 230 and the dummy pixel 247 of the light receiving unit 23, so that the vertical scanning unit 241 transfers the imaging signal, the dummy signal, and a noise signal that are present when the pixels are reset, to a vertical transfer line 239 (first transfer line) and outputs these signals to the noise removing unit 243.

The noise removing unit 243 removes output variations of each of the unit pixels 230 and the noise signal that are present when the pixels are reset and outputs the imaging signal photoelectrically converted by each of the unit pixels 230. Details of the noise removing unit 243 will be described later.

The horizontal scanning unit 245 applies a drive signal ΦHCLK<N> to a selected column (vertical line) <N> (N=0, 1, 2, ..., n-1, and n) of the light receiving unit 23, based on a drive signal (ΦHCLK) supplied from the timing generator 25. Then, the horizontal scanning unit 245 transfers the imaging signal photoelectrically converted by each of the unit pixels 230 to a horizontal transfer line 258 (second transfer line) through the noise removing unit 243, and outputs the imaging signal to the output unit 31. In the first embodiment, the horizontal transfer line 258 functions as a transfer unit that transfers the imaging signal outputted from each of the unit pixels 230.

In the light receiving unit 23 of the first chip 21, a large number of unit pixels 230 are arranged in a two-dimensional matrix form. Each of the unit pixels 230 includes a photoelectric conversion element 231 (photodiode), a charge converter 233, a transfer transistor 234 (first transfer unit), a pixel reset unit 236 (transistor), a pixel source follower transistor 237, and a dummy pixel 247 (reference signal generator). Herein, one or a plurality of photoelectric conversion elements and a transfer transistor for transferring a signal charge from each photoelectric conversion element to the charge converter 233 are referred to as a unit cell. In other words, the unit cell includes one or a plurality of pairs of the photoelectric conversion element and the transfer transistor and each of the unit pixels 230 includes one unit cell.

The photoelectric conversion element 231 photoelectrically converts incident light into a signal charge quantity according to a light quantity of the incident light and accumulates the signal charge quantity. The cathode of the photoelectric conversion element 231 is connected to one end of the transfer transistor 234 and the anode is connected to the ground GND. The charge converter 233 includes a floating diffusion capacitor (FD) and converts the charge accumulated by the photoelectric conversion element 231 into a voltage.

The transfer transistor 234 transfers a charge from the photoelectric conversion element 231 to the charge converter 233. A signal line that supplies the drive signal (row selection pulse) ΦR and the drive signal ΦT is connected to the gate of the transfer transistor 234 and the charge converter 233 is connected to the other end of the transfer transistor 234. When the drive signal ΦR and the drive signal ΦT are supplied to the transfer transistor 234 from the vertical scanning unit 241 through the signal line, the transfer transistor 234 turns on and transfers a signal charge from the photoelectric conversion element 231 to the charge converter 233.

The pixel reset unit 236 resets the charge converter 233 to a predetermined potential. One end of the pixel reset unit 236 is connected to a power supply voltage VR, the other end is connected to the charge converter 233, and the gate of the pixel reset unit 236 is connected to a signal line that supplies the drive signal ΦR. When the drive signal ΦR is supplied to the pixel reset unit 236 from the vertical scanning unit 241 through the signal line, the pixel reset unit 236 turns on, discharges a signal charge accumulated in the charge converter 233, and resets the charge converter 233 to a predetermined potential.

One end of the pixel source follower transistor 237 is connected to the power supply voltage VR, the other end is connected to the vertical transfer line 239, and a signal converted into a voltage by the charge converter 233 (the imaging signal or a signal at time of reset) is input into the gate of the pixel source follower transistor 237. When the drive signal ΦT is supplied to the gate of the transfer transistor 234 following a selection operation, which will be described later, of the pixel source follower transistor 237, a charge is read from the photoelectric conversion element 231, converted into a voltage by the charge converter 233, and then transferred to the vertical transfer line 239 through the pixel source follower transistor 237.

The dummy pixels 247 are provided for each vertical line of the unit pixels 230 at the same pitch as that of the unit pixels 230. The dummy pixel 247 includes a pixel reset unit 236a and a pixel source follower transistor 237a. In other words, the dummy pixel 247 has a configuration in which the photoelectric conversion element 231 (photodiode), the charge converter 233, and the transfer transistor 234 (first transfer unit) are removed from the unit pixels 230.

The pixel reset unit 236a resets the gate of the pixel source follower transistor 237a to a predetermined potential. One end of the pixel reset unit 236a is connected to the power supply voltage VR, the other end is connected to the gate of the pixel source follower transistor 237a, and the gate of the pixel reset unit 236a is connected to a signal line that supplies the drive signal ΦRdmy.

When the drive signal ΦRdmy is supplied to the gate of the pixel reset unit 236a from the timing generator 25 through the signal line, the pixel reset unit 236a turns on and the gate of the pixel source follower transistor 237a is fixed to a predetermined potential (VRdmy).

One end of the pixel source follower transistor 237a is connected to the power supply voltage VR supplied from the reference voltage generator 246 (reference voltage generator 246a illustrated in FIG. 5A), the other end is connected to the vertical transfer line 239, and a predetermined potential (VRdmy) is input into the gate of the pixel source follower transistor 237a. When a selection operation, which will be described later, is performed on the pixel source follower transistor 237a configured as described above, a dummy signal (column reference signal) according to the predetermined potential (VRdmy) is transferred to the vertical transfer line 239 through the pixel source follower transistor 237a.

In the same manner as in a normal unit pixels 230, in the first embodiment, when the drive signal ΦRdmy is supplied to the gate of the pixel reset unit 236a upon inputting VRdmy (for example, 2 V) while the power supply voltage VR is at a power supply voltage VDD level (for example, 3.3 V), the pixel source follower transistor 237a turns on and the dummy pixel 247 including the pixel reset unit 236a is selected (selection operation). When the drive signal ΦRdmy is supplied to the gate of the pixel reset unit 236a when the power supply voltage VR is a non-selection voltage level (for example, 1 V) and VRdmy (for example, 1 V) is input, the pixel source follower transistor 237a becomes an off state and the selection of the dummy pixel 247 including the pixel reset unit 236a is released (non-selection operation).

One end of the constant current source 242 is connected to the vertical transfer line 239, the other end is connected to the ground GND, and a bias voltage Vbias1 is applied to the gate of the constant current source 242. The constant current source 242 drives the unit pixels 230 by the constant current source 242 and reads the output of the unit pixels 230 to the vertical transfer line 239. A signal read to the vertical transfer line 239 is input into the noise removing unit 243.

The noise removing unit 243 includes a transfer capacitor 252 (AC coupling capacitor) and a clamp switch 253 (transistor).

One end of the transfer capacitor 252 is connected to the vertical transfer line 239 and the other end is connected to the column source follower transistor 244.

One end of the clamp switch 253 is connected to a signal line to which a clamp voltage Vclp is supplied from the reference voltage generator 246. The other end of the clamp switch 253 is connected to between the transfer capacitor 252 and the column source follower transistor 244 and a drive signal ΦVCL is input into the gate from the timing generator 25. The imaging signal input into the noise removing unit 243 is an optical noise sum signal including a noise component.

When the drive signal ΦVCL is input into the gate of the clamp switch 253 from the timing generator 25, the clamp switch 253 turns on and the transfer capacitor 252 is reset by the clamp voltage Vclp supplied from the reference voltage generator 246. The imaging signal from which noise has been removed by the noise removing unit 243 is input into the gate of the column source follower transistor 244.

The noise removing unit 243 does not require a capacitor for sampling (a sampling capacitor), so that the capacity of the transfer capacitor 252 (AC coupling capacitor) only has to be a capacity sufficient for the input capacity of the column source follower transistor 244. In addition, since the noise removing unit 243 does not include a sampling capacitor, it is possible to reduce the occupied area of the noise removing unit 243 in the first chip 21.

One end of the column source follower transistor 244 is connected to the power supply voltage VDD, the other end is connected to one end of a column selection switch 254 (second transfer unit), and the imaging signal from which noise has been removed by the noise removing unit 243 is input into the gate of the column source follower transistor 244.

One end of the column selection switch 254 is connected to the other end of the column source follower transistor 244, the other end of the column selection switch 254 is connected to the horizontal transfer line 258 (second transfer line), and a signal for supplying a drive signal ΦHCLK<N> from the horizontal scanning unit 245 is connected to the gate of the column selection switch 254. When the drive signal ΦHCLK<N> is supplied to the gate of the column selection switch 254 of a column <N> from the horizontal scanning unit 245, the column selection switch 254 turns on and transfers a signal of the vertical transfer line 239 of the column <N> (the imaging signal from which noise has been removed by the noise removing unit 243) to the horizontal transfer line 258.

One end of a horizontal reset transistor 256 is connected to the ground GND, the other end is connected to the horizontal transfer line 258, and a drive signal ΦHCLR is input into the gate of the horizontal reset transistor 256 from the timing generator 25. When the drive signal ΦHCLR is input into the gate of the horizontal reset transistor 256 from the timing generator 25, the horizontal reset transistor 256 turns on and resets the horizontal transfer line 258.

One end of a constant current source 257 is connected to the horizontal transfer line 258, the other end is connected to the ground GND, and a bias voltage Vbias2 is applied to the gate of the constant current source 257. The constant current source 257 reads the imaging signal from the vertical transfer line 239 to the horizontal transfer line 258. The imaging signal or the dummy signal read to the horizontal transfer line 258 is input into the output unit 31.

The output unit 31 outputs the imaging signal from which noise has been removed and the dummy signal (a reference signal to be a reference when correcting a vertical line) by amplifying the signals as needed (Vout).

In the first embodiment, reading of the imaging signal, from which noise has been removed, from the vertical transfer line 239, and resetting of the horizontal transfer line 258 by the horizontal reset transistor 256 are alternately performed, so that it is possible to suppress crosstalk of the imaging signal in a column direction.

In the second chip 22, the dummy signal and the imaging signal are transmitted to the connector unit 5 through the transmission cable 3.

Figure 5A:
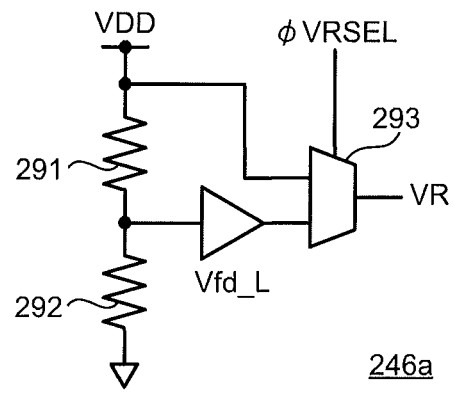
FIG. 5A is a circuit diagram illustrating a configuration of a reference voltage generator of the endoscope system according to the first embodiment of the present invention.
Figure 5B:
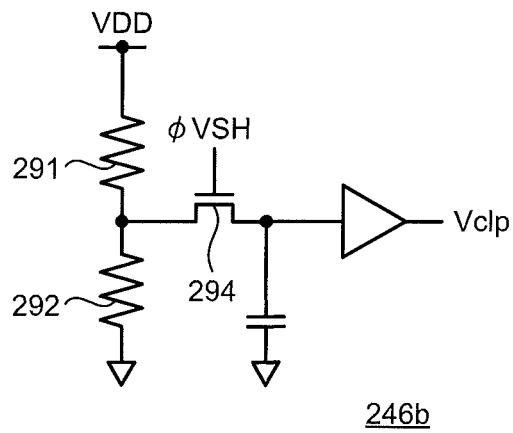
FIG. 5B is a circuit diagram illustrating a configuration of a reference voltage generator of the endoscope system according to the first embodiment of the present invention.

FIGS. 5A and 5B are circuit diagrams illustrating a configuration of the reference voltage generator 246 of the light receiving unit 23 of the endoscope system 1 according to the first embodiment.

A reference voltage generator 246a illustrated in FIG. 5A includes a resistance voltage dividing circuit consisting of two resistors 291 and 292, and a multiplexer 293 that is driven by a drive signal ΦVRSEL.

The multiplexer 293 applies the power supply voltage VDD (for example, 3.3 V) and a non-selection voltage Vfd_L (for example, 1 V) generated by the resistance voltage dividing circuit to all the pixels and the dummy pixels 247, as the power supply voltage VR, while alternately switching the power supply voltage VDD and the non-selection voltage Vfd_L, according to the drive signal ΦVRSEL input from the timing generator 25.

A reference voltage generator 246b illustrated in FIG. 5B includes a resistance voltage dividing circuit consisting of two resistors 291 and 292, and a switch (transistor) 294 that is driven by a drive signal ΦVSH. The reference voltage generator 246b generates the clamp voltage Vclp of the noise removing unit 243 at a timing when the drive signal ΦVSH is driven by driving the switch 294.

Processing of Endoscope

Figure 6:
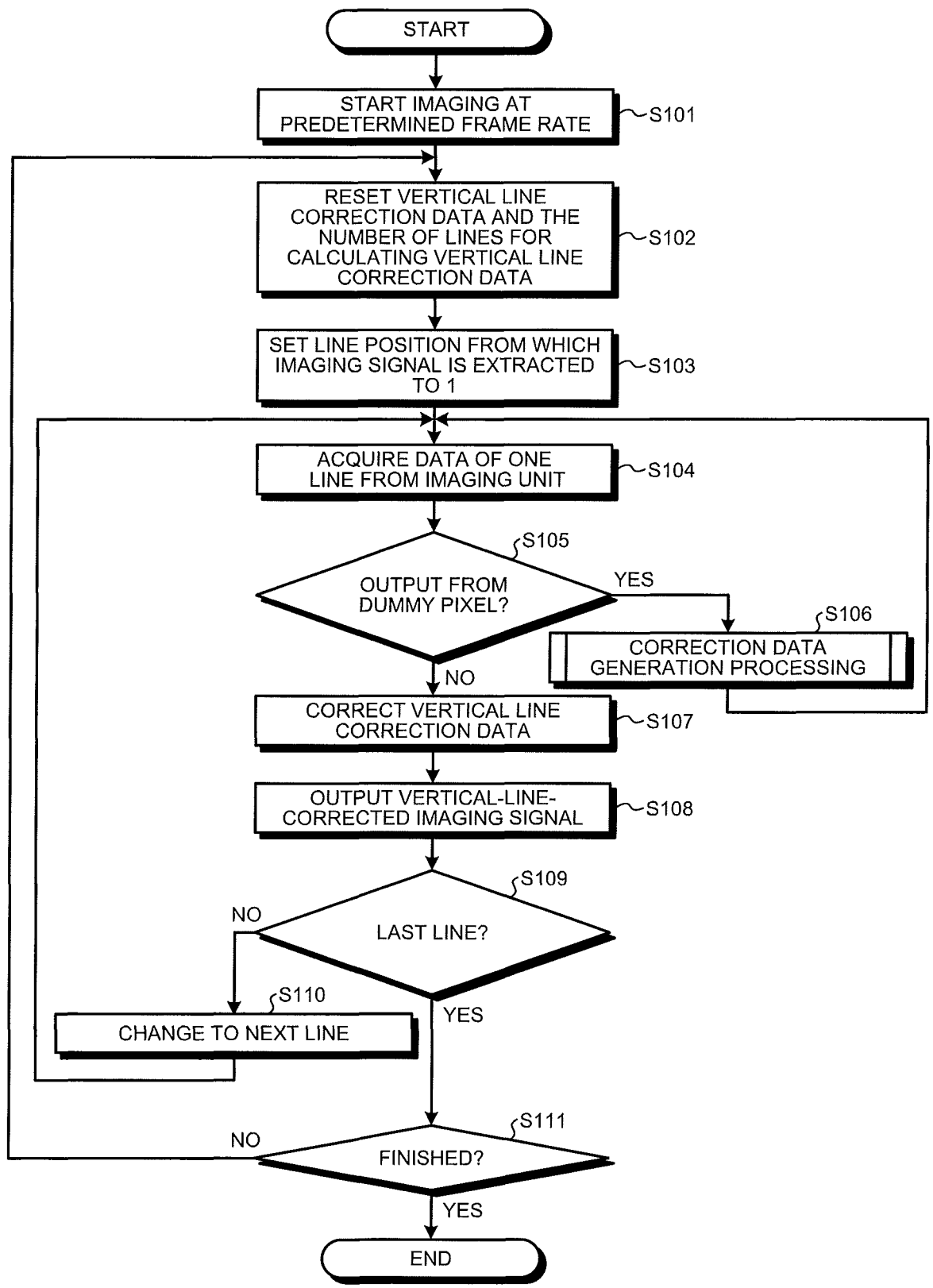
FIG. 6 is a flowchart illustrating an overview of processing performed by an endoscope according to the first embodiment of the present invention.

Next, processing performed by the endoscope 2 will be described. FIG. 6 is a flowchart illustrating an overview of the processing performed by the endoscope 2.

As illustrated in FIG. 6, first, the imaging unit 20 starts imaging at a predetermined frame rate based on a reference clock signal generated by the drive signal generator 54 (step S101).

Subsequently, the imaging signal processing unit 52 resets vertical line correction data and the number of lines for calculating the vertical line correction data (step S102) and sets a line position from which the imaging signal is extracted to 1 (step S103).

Subsequently, the imaging signal processing unit 52 acquires data of one line of image data from the imaging unit 20 through the AFE unit 51 (step S104).

Thereafter, when the data of one line of image data acquired from the imaging unit 20 is an output from the dummy pixel 247 (step S105: Yes), the endoscope 2 performs, based on the dummy signal outputted from the dummy pixel 247, correction data generation processing that generates correction data used for correction processing that corrects a vertical line of the imaging signal (step S106). After step S106, the endoscope 2 returns to step S104.

Figure 7:
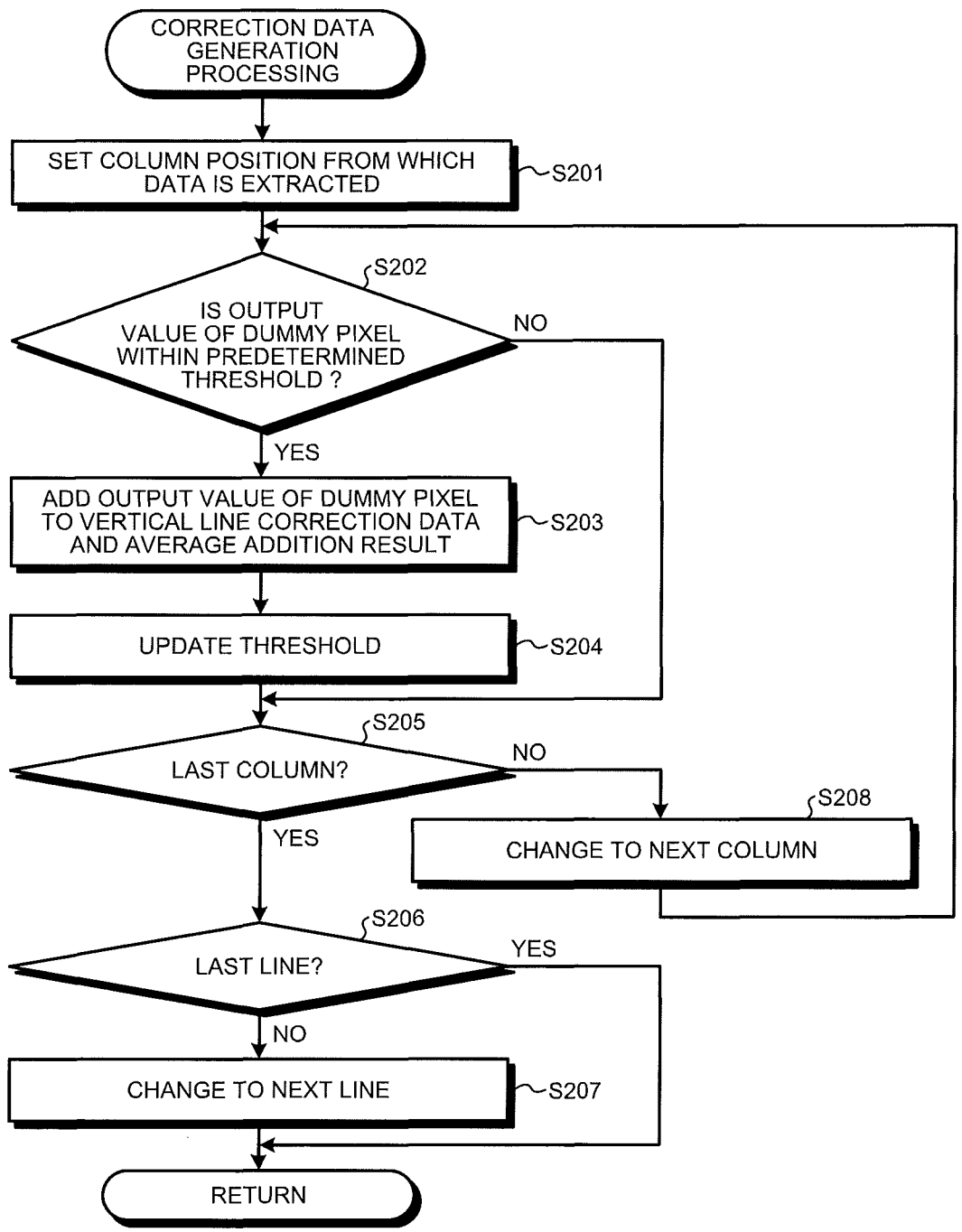
FIG. 7 is a flowchart illustrating an overview of correction data generation processing in FIG. 6.

FIG. 7 is a flowchart illustrating an overview of the correction data generation processing. As illustrated in FIG. 7, first, the imaging signal processing unit 52 sets a column position from which data is extracted from the light receiving unit 23 (step S201). For example, the imaging signal processing unit 52 sets a column position (horizontal line) of line data read from the imaging unit 20 to "1".

Subsequently, the determination unit 521 determines whether or not an output value of the dummy pixel 247 is within a predetermined threshold (step S202). Specifically, the determination unit 521 determines whether or not the output value of the dummy pixel 247 is within a range of threshold recorded by the threshold data recording unit 531. When the determination unit 521 determines that the output value of the dummy pixel 247 is within the predetermined threshold (step S202: Yes), the endoscope 2 proceeds to step S203 described below. On the other hand, when the determination unit 521 determines that the output value of the dummy pixel 247 is not within the predetermined threshold (step S202: No), the endoscope 2 proceeds to step S205 described below.

Figure 8A:
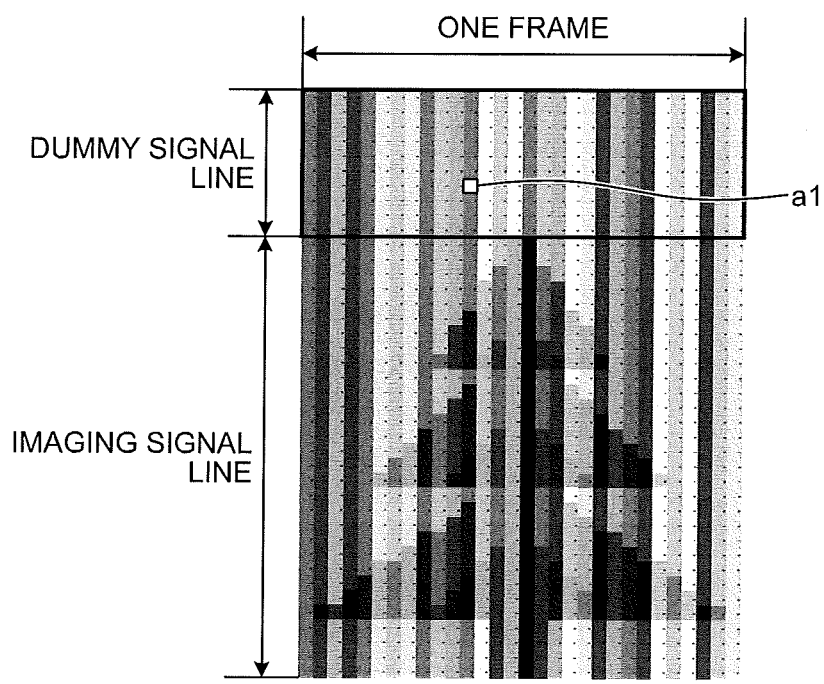
FIG. 8A is a conceptual diagram illustrating an output format outputted by the first chip of the endoscope according to the first embodiment of the present invention.

In step S203, the correction data generator 522 adds the output value from the dummy pixel 247 to a corresponding column of vertical line correction data recorded by the correction data recording unit 532 and averages the addition result (step S203). Specifically, the correction data generator 522 adds the output value of a dummy signal that is output this time, to output values of dummy signals acquired from the dummy pixel 247 a plurality of times, which are recorded by the correction data recording unit 532, and divides the sum by the number of times of the addition of the output values of the dummy signals, thereby generating correction data for correcting a vertical line. In other words, the correction data generator 522 generates correction data for each vertical line by using only the output values of dummy signals which have been determined to be within a predetermined threshold by the determination unit 521. Thereby, as illustrated in FIG. 8A, when the correction unit 523 corrects a vertical line of the imaging signal from the imaging unit 20 by using the correction data, it is possible to remove an output value a1 of a dummy signal on which noise and the like are superimposed, so that it is possible to generate accurate correction data. FIG. 8A is a conceptual diagram illustrating an output format outputted by the first chip 21. FIG. 8A illustrates an array in which the unit pixels of the effective pixel area are 30×30. The number of output times from the dummy pixel 247 is 10. Of course, it is possible to appropriately change the number of output times from the dummy pixel 247.

Subsequently, the correction data generator 522 adds the output value from the dummy pixel 247 to the threshold of corresponding vertical line recorded by the threshold data recording unit 531, and calculates an average value by dividing the sum by the number of times of the addition of the output values of the dummy signals, thereby updating the threshold (step S204).

Subsequently, in a case in which the last column of one line of image data acquired from the imaging unit 20 is processed (step S205: Yes), when the one line of image data acquired from the imaging unit 20 is the last line (step S206: Yes), the endoscope 2 returns to main routine in FIG. 6. On the other hand, in a case in which the last column of one line of image data acquired from the imaging unit 20 is processed (step S205: Yes), when the one line of image data acquired from the imaging unit 20 is not the last line (step S206: No), the imaging signal processing unit 52 changes a line from which data is acquired from the imaging unit 20 to the next line (step S207). After step S207, the endoscope 2 returns to main routine in FIG. 6.

In step S205, when the last column of one line of image data acquired from the imaging unit 20 is not processed (step S205: No), the imaging signal processing unit 52 changes the process to the next column of one line of image data acquired from the imaging unit 20 (step S208). After step S208, the endoscope 2 returns to step S202.

Let us return to FIG. 6. Step S105 and the following steps will be continuously described.

In step S105, when the data of one line acquired from the imaging unit 20 is not an output from the dummy pixel 247, that is, when the data is data from the unit pixels 230 (the imaging signal) (step S105: No), the endoscope 2 proceeds to step S107.

Figure 8B:
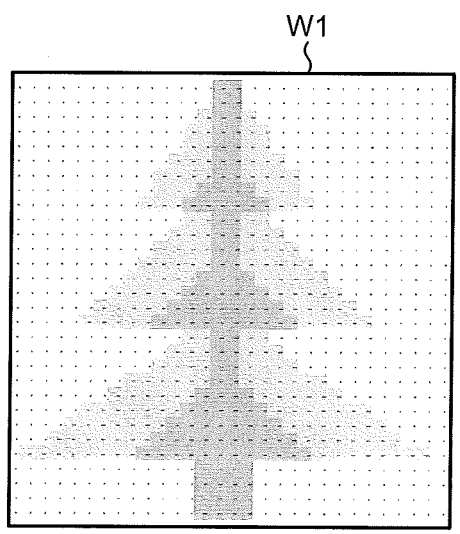
FIG. 8B is a diagram schematically illustrating an example of an image corrected by a correction unit of the endoscope according to the first embodiment of the present invention.

Subsequently, the correction unit 523 corrects the imaging signal by subtracting the vertical line correction data recorded by the correction data recording unit 532 from the imaging signal outputted from the unit pixels 230 (step S107) and transmits the vertical-line-corrected imaging signal to the image signal processing unit 62 (step S108). Specifically, as illustrated in FIGS. 8A and 8B, the correction unit 523 corrects the imaging signal outputted from the unit pixels 230 by subtracting the vertical line correction data recorded by the correction data recording unit 532 from the imaging signal outputted from the unit pixels 230 (FIG. 8A to FIG. 8B). Thereby, it is possible to accurately correct the imaging signal, so that it is possible to obtain a high-quality image W1.

Thereafter, when the last line of the light receiving unit 23 is processed (step S109: Yes), the endoscope 2 proceeds to step S111 described below. On the other hand, when the last line of the light receiving unit 23 is not processed (step S109: No), the endoscope 2 proceeds to step S110 described below.

In step S110, the timing generator 25 changes a line from which the imaging signal or the dummy signal is read to the next line. After step S110, the endoscope 2 returns to step S104.

In step S111, when ending the imaging of the subject (step S111: Yes), the endoscope 2 ends the processing. On the other hand, when not ending the imaging of the subject (step S111: No), the endoscope 2 returns to step S102.

According to the first embodiment described above, the correction data generator 522 generates the correction data for each vertical line by using the statistic of output values of dummy signals, which have been determined to be within the predetermined range by the determination unit 521, for each vertical line, so that the correction unit 523 can accurately corrects the imaging signal of the unit pixels 230 in the effective pixel area.

According to the first embodiment, the correction data generator 522 and the correction unit 523 is provided in the connector unit 5, so that it is not necessary to provide the correction data in the processor 6 for each different type of endoscope. Therefore, the first embodiment is excellent in versatility.

In the first embodiment, the correction data generator 522 calculates an average value for each vertical line of output values of the dummy signals, which have been output from the dummy pixel 247 a plurality of times, as the statistic. However, for example, it is possible to generate correction data by calculating either one of a median value and a mode value as the statistic for each vertical line of output values of the dummy signals which have been output from the dummy pixel 247 a plurality of times.

Further, in the first embodiment, when the determination unit 521 determines that each of output values of the dummy signals, which have been output a plurality of times from the dummy pixel 247, is not within a predetermined range, that is, when none of the dummy signals which have been output a plurality of times from the dummy pixel 247 is not within a predetermined range, it is possible to calculate the statistic by using output values of dummy signals outputted a plurality of times from an adjacent dummy pixel 247 to the dummy pixel 247 and generate correction data for correcting the imaging signal based on the statistic.

Second Embodiment

Next, a second embodiment of the present invention will be described. An endoscope system according to the second embodiment has the same configuration as that of the endoscope system 1 according to the first embodiment described above, and correction data generation processing performed by the endoscope 2 is different from that of the first embodiment. Therefore, in the description below, the correction data generation processing performed by the endoscope according to the second embodiment will be described. The same elements as those of the endoscope system 1 according to the first embodiment are denoted by the same reference signs and the explanation thereof will not be repeated.

Figure 9:
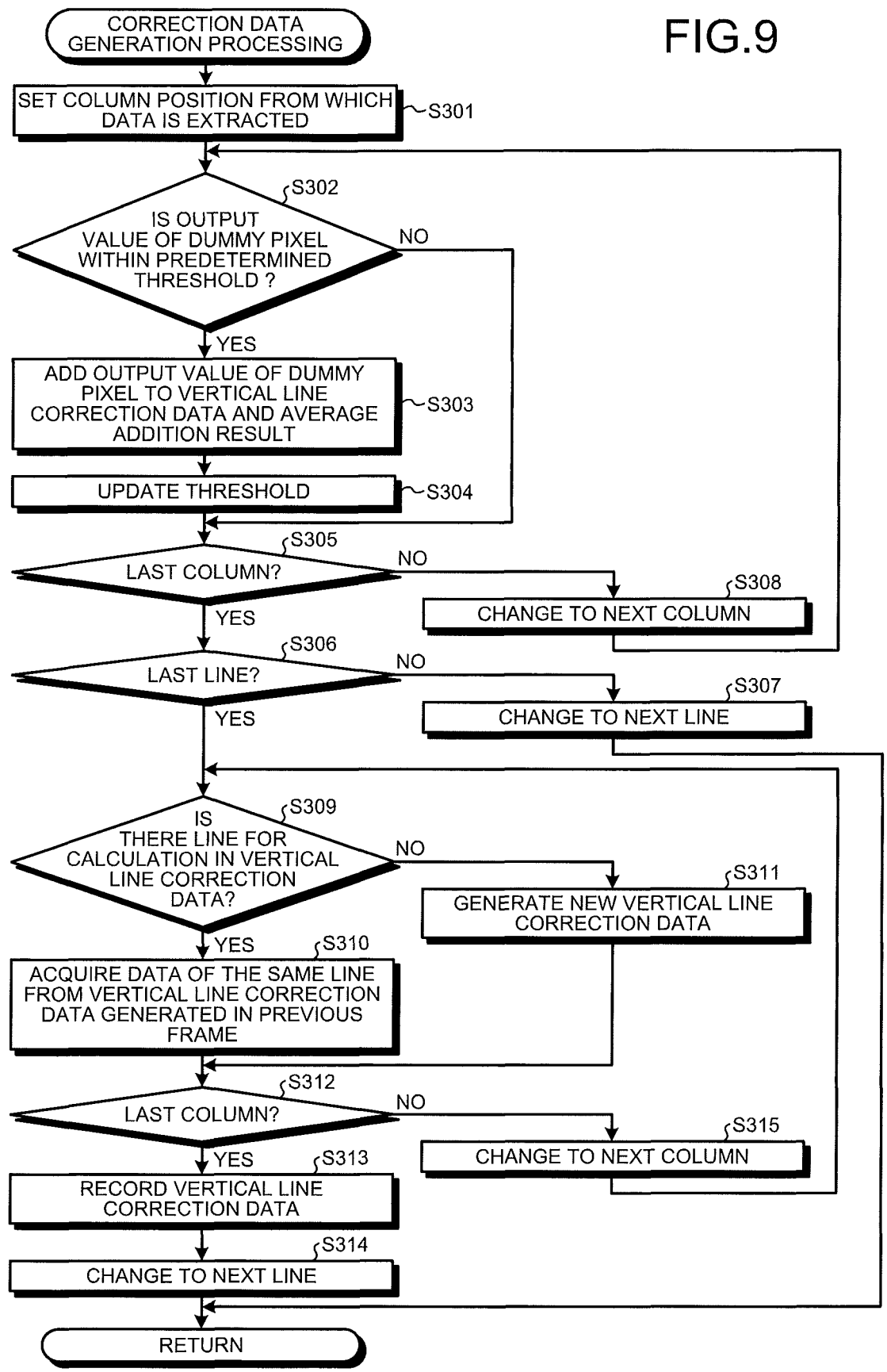
FIG. 9 is a flowchart illustrating an overview of correction data generation processing performed by an endoscope according to a second embodiment of the present invention.

FIG. 9 is a flowchart illustrating an overview of the correction data generation processing performed by the endoscope 2 according to the second embodiment.

As illustrated in FIG. 9, steps S301 to S308 respectively correspond to steps S201 to S208 of FIG. 7 described above.

In step S309, when there is a line for calculation in vertical line correction data generated by the correction data generator 522 (step S309: Yes), the correction data generator 522 acquires data of the same line from vertical line correction data generated by the correction data generator 522 in a previous frame which is recorded by the correction data recording unit 532 (step S310). After step S310, the endoscope 2 proceeds to step S312 described below.

In step S309, when there is not a line for calculation in vertical line correction data generated by the correction data generator 522 (step S309: No), the correction data generator 522 generates a new vertical line correction data by dividing vertical line correction data recorded by the correction data recording unit 532 by the number of lines for calculating the vertical line correction data (step S311). After step S311, the endoscope 2 proceeds to step S312 described below.

In step S312, when one line of image data acquired from the imaging unit 20 is the last column (step S312: Yes), the correction data generator 522 records the vertical line correction data generated in step S310 or step S311 described above into the correction data recording unit 532 (step S313).

Subsequently, the imaging signal processing unit 52 changes the line of image data to be acquired from the imaging unit 20 to the next line (step S314). After step S314, the endoscope 2 returns to the main routine in FIG. 6.

In step S312, when one line of image data acquired from the imaging unit 20 is not the last column (step S312: No), the imaging signal processing unit 52 changes the column to the next column in the one line of image data acquired from the imaging unit 20 (step S315). After step S315, the endoscope 2 returns to step S309.

According to the second embodiment described above, the correction data recording unit 532 is provided which records output values of dummy signals having been determined to be within a predetermined range by the determination unit 521, for each frame in which each of a plurality of unit pixels 230 generates an imaging signal. When the determination unit 521 determines that each of output values of dummy signals outputted a plurality of times from the dummy pixel 247 is not within a predetermined range, the correction data generator 522 acquires, from the correction data recording unit 532, an output value that is output by the dummy pixel 247 in a previous frame and generates correction data, so that even when, for example, RTS noise occurs, the correction unit 523 can accurately correct the imaging signal of the unit pixels 230 in the effective pixel area. Therefore, it is possible to obtain a high-quality image.

Third Embodiment

Next, a third embodiment of the present invention will be described. An endoscope system according to the third embodiment is different from the endoscope system 1 according to the first embodiment described above in a configuration of the first chip 21 of the endoscope 2. Specifically, the first chip 21 according to the first embodiment described above is provided with the vertical transfer line 239 for each column of the unit pixels 230. However, the first chip according to the third embodiment reads the imaging signal of two unit pixels 230 adjacent to each other by one vertical transfer line (pixel sharing). Therefore, in the description below, the configuration of the first chip according to the third embodiment will be described. The same elements as those of the endoscope system 1 according to the first embodiment are denoted by the same reference signs and the explanation thereof will be omitted.

Configuration of First Chip

Figure 10:
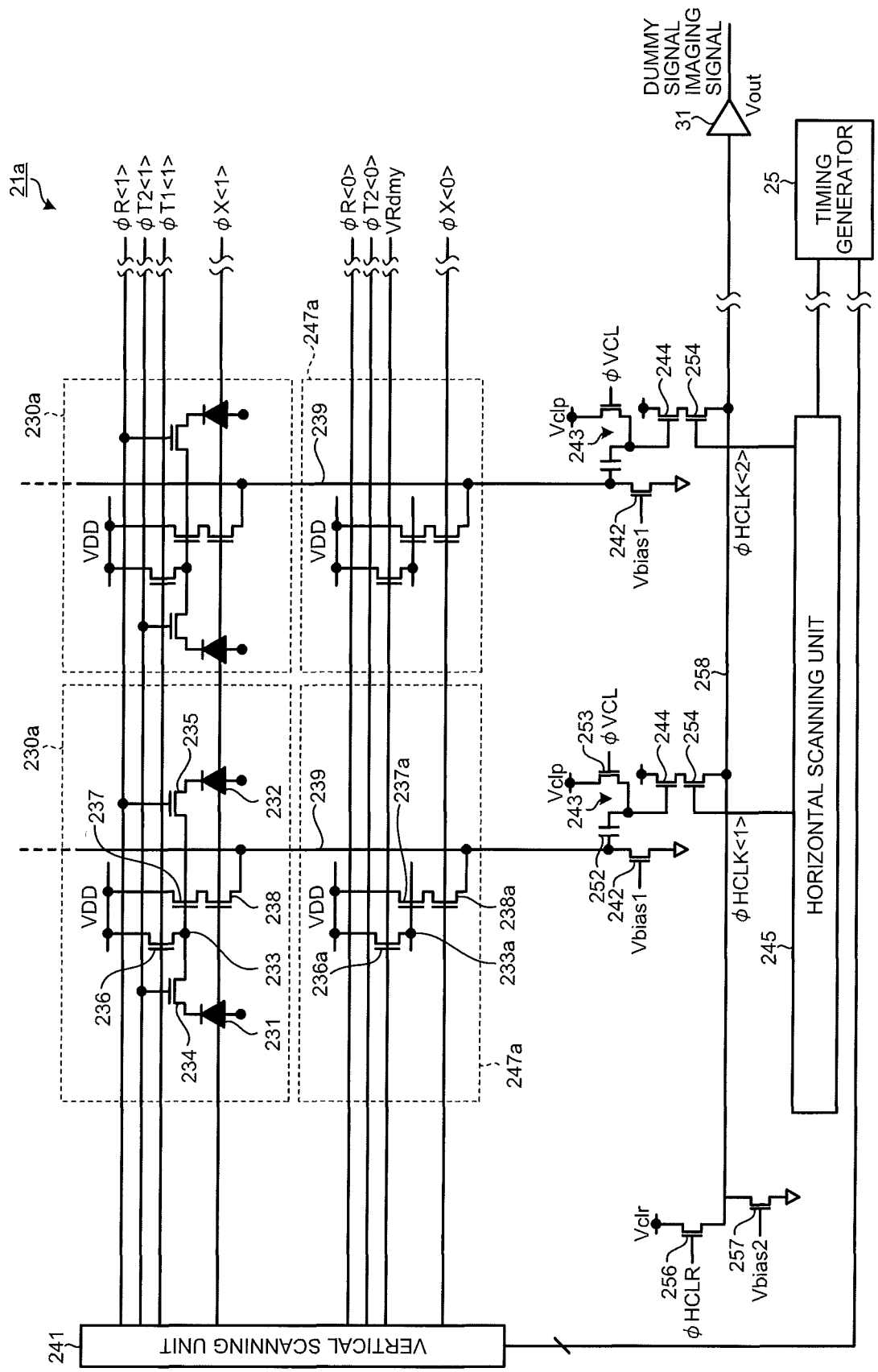
FIG. 10 is a circuit diagram illustrating a configuration of a first chip of an endoscope according to a third embodiment of the present invention.

FIG. 10 is a circuit diagram illustrating the configuration of the first chip according to the third embodiment. A first chip 21a illustrated in FIG. 10 has unit pixels 230a and dummy pixels 247a instead of the unit pixels 230 and the dummy pixels 247 of the configuration of the first chip 21 described above.

The unit pixels 230a includes a photoelectric conversion element 231, a photoelectric conversion element 232, a charge converter 233, a transfer transistor 234, a transfer transistor 235, a pixel reset unit 236, a pixel source follower transistor 237, and a pixel output switch 238.

The photoelectric conversion element 232 photoelectrically converts incident light into a signal charge quantity according to a light quantity of the incident light and accumulates the signal charge quantity. The cathode of the photoelectric conversion element 232 is connected to one end of the transfer transistor 235 and the anode is connected to the ground GND. The charge converter 233 includes a floating diffusion capacitor (FD) and converts the charge accumulated by the photoelectric conversion element 231 and the photoelectric conversion element 232 into a voltage.

The transfer transistor 235 transfers a charge from the photoelectric conversion element 232 to the charge converter 233. A signal line that supplies pulse-shaped drive signals (row selection pulses) $\Phi T1$ and $\Phi T2$ is connected to the gate of the transfer transistor 235, and the other end is connected to the charge converter 233. When the pulse-shaped drive signals $\Phi T1$ and $\Phi T2$ are supplied from the vertical scanning unit 241 through the signal line, the transfer transistors 234 and 235 become an on state and a signal charge is transferred from the photoelectric conversion element 232 to the charge converter 233.

The pixel output switch 238 outputs a signal, which has been converted into a voltage by the charge converter 233, to the vertical transfer line 239. The other end of the pixel output switch 238 is connected to the vertical transfer line 239, and a signal line that supplies a pulse-shaped drive signal ΦX is connected to the gate of the pixel output switch 238. When the pulse-shaped drive signal ΦX is supplied to the gate of the pixel output switch 238 from the vertical scanning unit 241 through a pixel drive line, the pixel output switch 238 turns on and the imaging signal or a signal at time of reset is transferred to the vertical transfer line 239.

The dummy pixel 247a is provided for each column of unit pixels 230a and the dummy pixels 247a are provided at the same pitch as that of the unit pixels 230a. The dummy pixel 247a includes a charge converter 233a, a pixel reset unit 236a, a pixel source follower transistor 237a, and a pixel output switch 238a. In other words, the dummy pixel 247a has a configuration in which the photoelectric conversion element 231, the photoelectric conversion element 232, the transfer transistor 234, and the transfer transistor 235 are removed from the unit pixels 230a.

The pixel output switch 238a outputs a signal, which has been converted into a voltage by the charge converter 233a, to the vertical transfer line 239. The other end of the pixel output switch 238a is connected to the vertical transfer line 239, and a signal line that supplies the pulse-shaped drive signal ΦX is connected to the gate of the pixel output switch 238a. When the pulse-shaped drive signal ΦX is supplied to the gate of the pixel output switch 238a from the vertical scanning unit 241 through a pixel drive line, the pixel output switch 238a turns on and the imaging signal or a signal at time of reset is transferred to the vertical transfer line 239.

Figure 11:
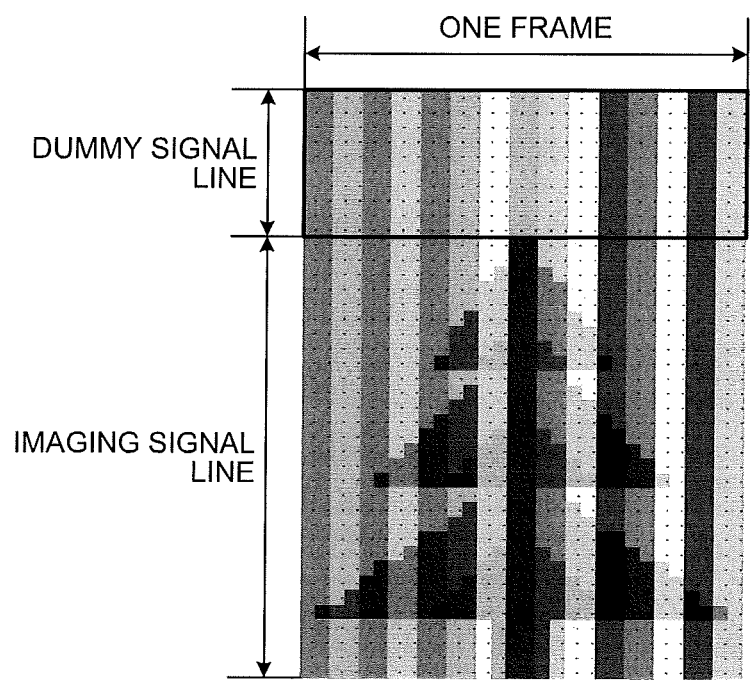
FIG. 11 is a conceptual diagram illustrating an output format outputted by the first chip of the endoscope according to the third embodiment of the present invention.

By using the first chip 21a configured as described above, the correction unit 523 of the endoscope 2 corrects the imaging signal outputted from the unit pixels 230a by subtracting the vertical line correction data recorded by the correction data recording unit 532 from the imaging signal outputted from the unit pixels 230a by performing the same processing as that of the first embodiment or the second embodiment described above (FIG. 11 to FIG. 8B). Thereby, even when the imaging signal is read from two photoelectric conversion elements 231 and 232 (pixels) adjacent to each other through one vertical transfer line 239, it is possible to accurately correct the imaging signal, so that it is possible to obtain a high-quality image.

According to the third embodiment described above, in the same manner as in the first embodiment described above, the correction data generator 522 generates the correction data for each vertical line by using the statistic of output values of dummy signals, which have been determined to be within the predetermined range by the determination unit 521, for each vertical line, so that the correction unit 523 can accurately corrects the imaging signal of the unit pixels 230a in the effective pixel area.

Other Embodiments

In the embodiments described above, the correction data generator 522 and the correction unit 523 are provided in the connector unit 5 of the endoscope 2. However, the correction data generator 522 and the correction unit 523 may be provided in the operating unit 4 of the endoscope 2.

The embodiments described above are applied to an endoscope to be inserted into a subject. However, the embodiments can also be applied to, for example, a capsule-shaped endoscope.

In the embodiments described above, the correction data generator 522 and the correction unit 523 are provided in the connector unit 5 of the endoscope 2. However, the correction data generator 522 and the correction unit 523 may be provided in the processor 6.

In the description of the flowcharts herein, the processing sequence of steps is clarified by using the terms such as "first", "thereafter" and "subsequently". However, the sequence of the processing required to implement the present invention is not uniquely determined by these terms. That is to say, the sequence of the processing in the flowcharts herein can be changed in a range without contradiction.

According to some embodiments, it is possible to accurately correct the output value of the effective pixel area.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
    an image sensor comprising:
        a plurality of pixels arranged in a two-dimensional matrix form and configured to receive light from outside, generate an imaging signal according to an amount of received light, and output the imaging signal through one of a plurality of vertical lines in the plurality of pixels, each two pixels adjacent to one another in a horizontal direction among the plurality of pixels sharing a single vertical line of the plurality of vertical lines; and
        a plurality of dummy pixels, each of which is provided for each of the plurality of vertical lines in the plurality of pixels, the plurality of dummy pixels being configured to generate and output a dummy signal to be used for correction processing of the imaging signal; and
    a processor comprising hardware, the processor being configured to:
        record a threshold;
        input dummy signals having been output a plurality of times from a dummy pixel of the plurality of dummy pixels and to determine whether or not each of output values of the input dummy signals is within a range of the recorded threshold;
        calculate, for each of the plurality of vertical lines, a statistic of the output values of the dummy signals determined to be within the range of the recorded threshold;
        generate, for each of the plurality of vertical lines, correction data for correcting the imaging signal generated by each two pixels sharing the single vertical line, based on a result of the calculation;
        generate a new threshold by adding the output values of the dummy signals that are determined to be within the range of the recorded threshold to the recorded threshold and dividing a sum of the new threshold and the recorded threshold by the number of times of the addition of the output values of the dummy signals;

record the new threshold for updating; and correct the imaging signal based on the generated correction data.

2. The endoscope according to claim 1, wherein the statistic is one of an average value, a median value, and a mode value of the output values of the dummy signals determined to be within the range of the threshold for each of the plurality of vertical lines.

3. The endoscope according to claim 1, wherein when the processor determines that each of the output values of the dummy signals having been output a plurality of times from the dummy pixel, is not within the range of the threshold, the processor is configured to calculate the statistic by using output values of dummy signals having been output a plurality of times from another dummy pixel adjacent to the dummy pixel, thereby to generate the correction data.

4. The endoscope according to claim 1, wherein the processer is further configured to record the output values of the dummy signals determined to be within the range of the threshold for each frame in which each of the plurality of pixels generates the imaging signal, wherein when the processor determines that each of the output values of the dummy signals having been output a plurality of times from the dummy pixel, is not within the range of the threshold, the processor is configured to acquire a recorded output value that is output by the dummy pixel in a previous frame and generate the correction data.

5. An endoscope system comprising:

the endoscope according to claim 1, wherein the processor comprises a first processor; and a second processor configured to convert the imaging signal into an image signal, wherein the first processor is configured to be connected to the second processor.

\* \* \* \* \*